United States Patent [19]

Sewell, Jr.

[11] Patent Number: 5,122,147
[45] Date of Patent: Jun. 16, 1992

[54] POLYP MARKING DEVICE AND METHOD

[76] Inventor: Frank K. Sewell, Jr., 1413 North Elm, Henderson, Ky. 42420

[21] Appl. No.: 681,091

[22] Filed: Apr. 5, 1991

[51] Int. Cl.⁵ ............................................. A61D 1/00
[52] U.S. Cl. ................... 606/110; 606/113; 606/116
[58] Field of Search ............................ 606/110–117, 606/136, 137, 186; 81/9.22

[56] References Cited

U.S. PATENT DOCUMENTS

| | | | |
|---|---|---|---|
| 2,679,249 | 5/1954 | Weihmann | 606/112 X |
| 3,566,873 | 3/1971 | Melges | 606/111 X |
| 3,633,584 | 1/1972 | Farrell | 606/116 |
| 3,739,784 | 6/1973 | Itoh | 606/113 |
| 3,835,859 | 9/1974 | Roberts et al. | 606/113 X |
| 4,488,550 | 12/1984 | Niemeijer | 606/116 |

OTHER PUBLICATIONS

The Surgical Clinics of North America, Dec. 1989, Dr. Kenneth Forde, pp. 1287–1306.
Endoscopic Marking of Colonic Lesions, J. L. Ponsky and J. F. King, Gastrointestinal Endoscopy, vol. 22, No. 1, 1975, pp. 42–43.
Localization of the Colonic Polypectomy Site, A. E. Dagradi, JAMA, vol. 262, No. 19, Nov. 17, 1989, p. 2748.
Preoperative Tattooing of Polypectomy Site, J. B. Poulard et al., Endoscopy 17 (1985).
India Ink Colonic Tattoo: blots on the record, Gastrointestinal Endoscopy, vol. 37, No. 1, 1991, p. 99.

*Primary Examiner*—Peter A. Aschenbrenner
*Attorney, Agent, or Firm*—Baker & Daniels

[57] ABSTRACT

Surgical method and instrument such as a snare or forceps clamps, which can be moved to a position to firmly grasp a polyp. A tissue marking agent is disposed on the surface of the instrument that contacts a polyp, and the marking agent is crushed against the polyp. The marking agent is absorbed by the polyp and stains the tissue from which the polyp projects, the assist in visualizing the polyp site if conventional surgery is later required. The method and device may optionally provide for cutting and removing of the polyp and for application of a hemostatic agent to the polyp base to minimize bleeding.

30 Claims, 7 Drawing Sheets

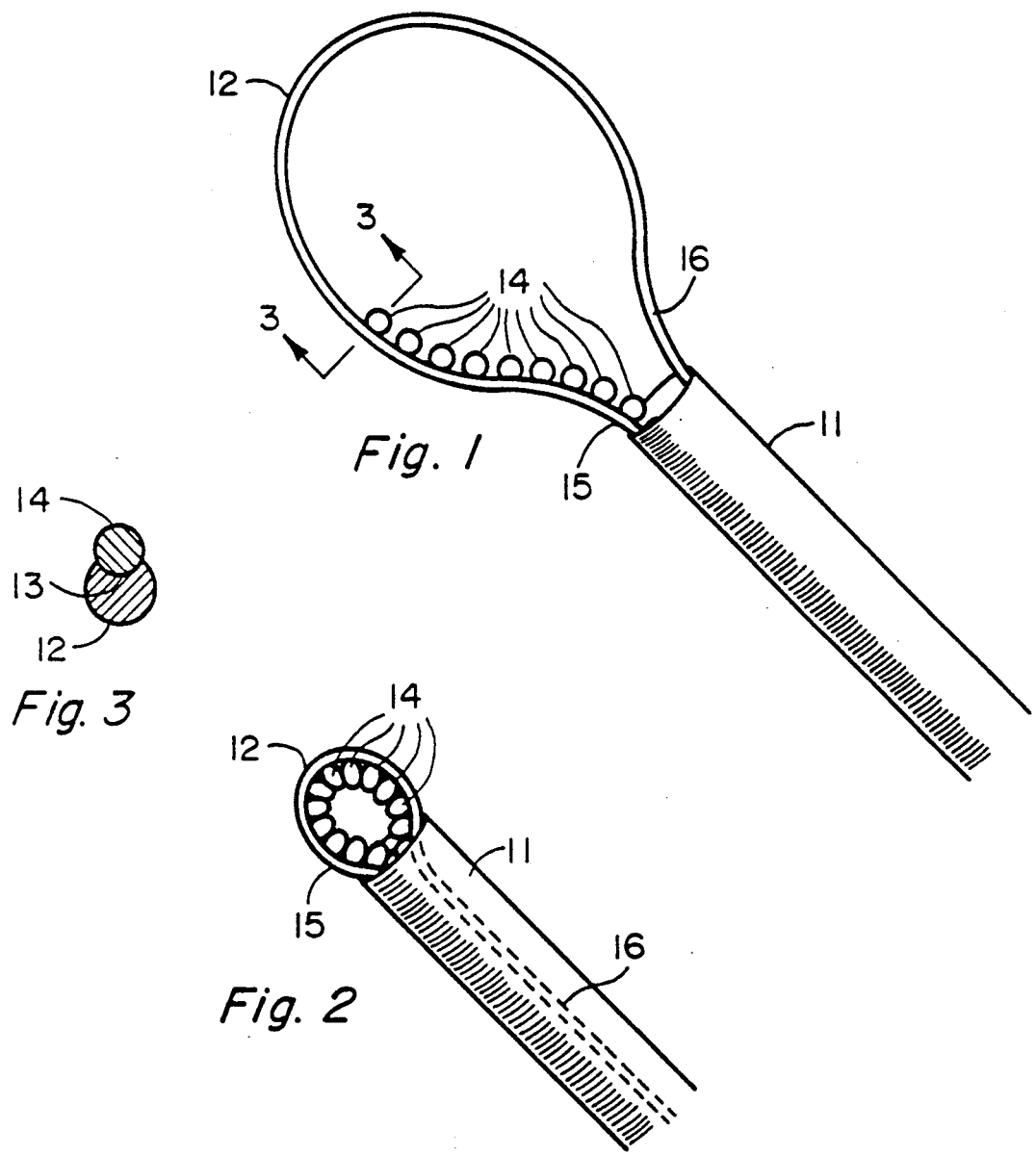

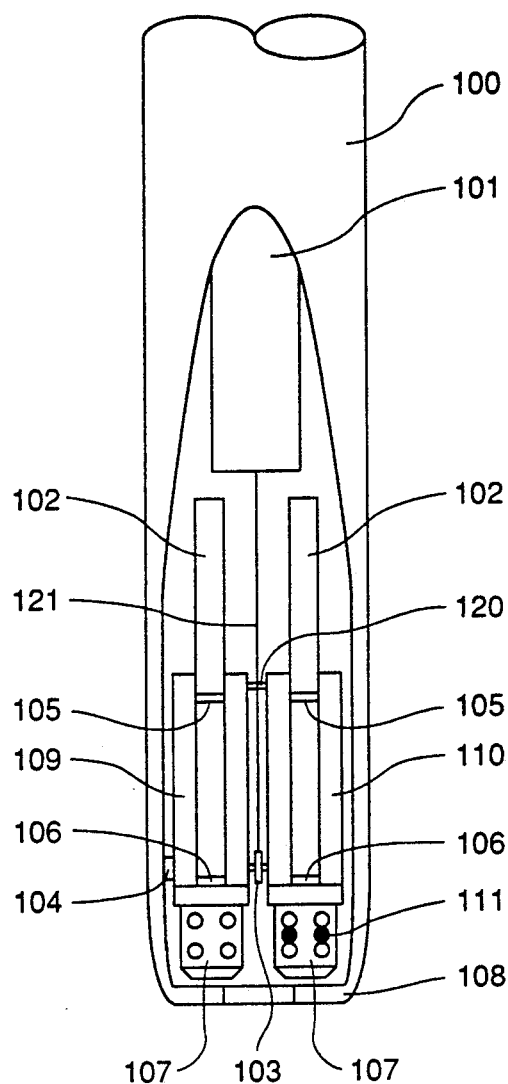
FIG. 9a
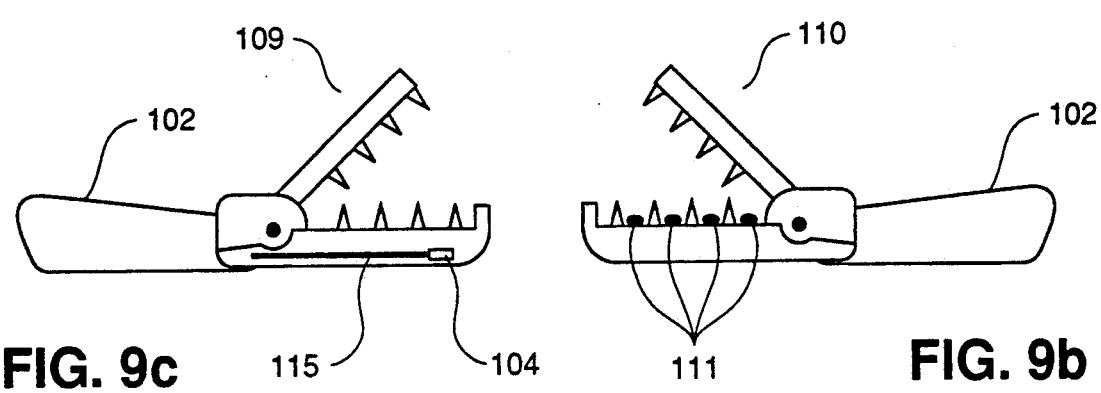
FIG. 9c  FIG. 9b

POLYP MARKING DEVICE AND METHOD

FIELD OF THE INVENTION

The present invention relates to devices for marking tissue, such as polyps, for surgery.

BACKGROUND OF THE INVENTION

Until about twenty-five years ago, treatment of polyps in internal organs, the colon for example, involved cutting through the abdominal wall, resecting an area of the colon and keeping the patient in the hospital until recovery from this major surgery. The only exceptions were polyps that were near the anus. After fiber optic filaments were invented, first diagnosis, and then treatment, was by the colonoscope. Colonoscopic polypectomy was introduced in 1969 and is considered relatively effective with a morbidity rate at present of 1% to 2.3% and a mortality rate of 0.01%. At present, the state of the art is to bite or snare the stalk of the polyp which crushes the tissue. After the physician decides that the tissue will not bleed significantly, he or she simply squeezes the forceps or snare further and pulls the specimen out. If the physician decides the tissue may bleed significantly, then an electrosurgical cautery unit provides a "coagulation" current. In actual fact, the current cauterizes all tissue, but coagulation does take place also.

Complications include bleeding, either immediately after the stalk is transected, or within twenty-four hours as crushed tissue moves, or a delayed hemorrhage up to two weeks after the cauterized eschar separates from the colonic wall. Accidental perforation of the colon occurs less frequently, but still up to 1% of the time. When colonic perforation does occur, it is usually results from the electrocautery. This can result from the electricity going via the blood vessels to the base of the polyp and the wall of the colon, the polyp head contacting the surrounding tissue, the cautery current being transmitted by a pool of fluid, the cautery current going through the head of the polyp to the opposite wall, the active electrode touching the surrounding tissue, and a pool of liquid reaching the metal inside the instrument, and so shorting out through the colonic wall. Also, the electrocautery current can short out through the patient or the endoscopist. Also perforation may be silent. A "post-polypectomy coagulation syndrome" almost certainly represents injury through the wall with microperforation. Actually, electrocautery is dangerous and in most hospitals is restricted to trained endoscopists who guard their privileges.

Other complications occurring during polypectomy include snare entrapment where the snare can neither be closed to transect the polyp nor opened to withdraw the snare. The snare and sheath may be left in place protruding from the rectum. Usually in one to three days, the snare can be disengaged without too much difficulty. The patients' comments about this complication are not well documented in the surgical literature.

Another complication is the lost polyp. The smaller polyp can be lost more easily and is harder to find. If the polyp is not found, one cannot simply wait for the patients to pass it with their stools. The polyp will autodigest, and become unsuitable for diagnostic purposes.

Perhaps the most frequent complication of the electrocautery is destruction of the tissue near the snare. The purpose of removing the polyp is to see if it is malignant. If the malignancy has invaded the stalk, one wants to know if all the cancer was removed during the procedure. Electrocautery usually makes exam by pathologists quite limited.

In addition, no list of complications would be complete without mentioning the infrequent, but always spectacular, explosions from a spark during the electrocauterization procedure. This event is a rather popular subject in surgical literature.

Another major complication is that often neither the endoscopist, the radiologist, or the surgeon, know exactly where the polyp was. The bowel both telescopes and stretches over the colonoscope so that measuring distances from the anal verge to the polyp using the colonoscope is notoriously inaccurate. Barium enemas are also inaccurate. The wall of the colon is made up of muscles and elastic tissue stretching and contracting all the time. Physicians have no way at the present time of precisely measuring exactly where a polyp is. The only exceptions are if it is very close to landmarks like the anal verge, appendix, splenic flexure, or hepatic flexure of the colon. The state of the art is for the surgeon to remove a segment of the colon which hopefully will include the polyp stalk. The colon segment is opened after it is removed, and an attempt is made to locate the stalk of the polyp. If the stalk is not located, then the surgeon either resects more colon with all the potential complications of doing this, or closes the abdominal wall and hopes the lost stalk of the polyp is really in the specimen and not in the patient.

In summary, endoscopic polypectomy is an inherently risky and intrinsically dangerous procedure which is made acceptable and relatively safe by skilled endoscopists.

Procedures for treating bleeding polyp stumps are known. In *The Surgical Clinics of North America*, December 1989, Dr. Kenneth Forde states that the bleeding polyp stump can be sprayed with iced saline or dilute epinephrine solution through a cannula in a colonoscope. However, commercially available colonoscopes are only 168 centimeters long, roughly six feet, so that the cannula would have to be longer, and such cannulas are not available. In addition, undue difficulty would be encountered in pushing a solution down a narrow column that long.

One technique for identifying a polyp stalk location during colonic resection is to first mark the stalk internally with a liquid dye or ink. The dye or ink will be transported to the colon wall and be visible from the outside of the colon during the resection surgery. This technique was reported by Jeffrey Ponsky, M.D., in 1975 in *Endoscopic Marking of Colonic Lesions*, 22 Gastrointestinal Endoscopy page 42, who used an Olympus NM-IK injection catheter to inject India ink and water into the mucosa of the colon. Therefore, such needles and tubes exist. The India ink marker is readily apparent on the serosal surface of the colon at a later laparotomy. In fact, Dr. Ponsky states it can be seen up to three weeks later. Dr. J. B. Poulard in *Pre-operative Tattooing of Polypectomy Site*, 17 Endoscopy 84 (1985) 1975, did the same thing also using an Olympus needle. He operated the next day and the India ink was readily apparent. Finally, in *Localization of the Colonic Polypectomy Site* 262 JAMA 2748 (Nov. 17, 1989), Dr. Angelo E. Gagardi of UCLA School of Medicine is asked how to localize a polypectomy site. He mentions tattooing the polypectomy site with India ink as a method for localizing the site. He states the stain may persist for longer than a month. However all such methods of employing a need to inject dye to localize a polypectomy site are inherently dangerous due the danger of the needle perforating the colon.

A number of U.S. patents disclose a variety of endoscopic forceps and tools for applying clips with penetrating teeth and large surface areas. U.S. Pat. No. 3,791,387 discloses a cutting snare forceps for excision and removal of polyps. A first wire extending through a rod as a snare may be retracted to sever a polyp. A second wire extends through the rod and attaches perpendicular to the first wire and when retracted serves to retain the severed polyp. U.S. Pat. No. 3,739,784 discloses a similar forceps but instead a wire may be adjacent to a blade. As the wire is retracted, the polyp is forced against the blade and thereby severed.

U.S. Pat. No. 3,828,790 discloses a surgical snare for polypectomies. The core of the snare is partially covered by a conductive wire presented as a spiral sleeve. The polyp is grasped with a snare with more control and decreased likelihood of accidental severing.

U.S. Pat. No. 2,571,908 discloses a surgical forceps in which the forceps when closed defines a chamber into which a severed mass of body tissue may be retained after cutting. U.S. Pat. No. 3,483,859 discloses a mechanism for marking a particular location of a body cavity, consisting of a string having an inflatable envelope thereon. A patient may swallow the device and then air may be pumped into the inflatable envelope. The exterior of the envelope contains an absorbent material which will absorb blood which may be located in an adjacent area. After the device is removed, the location of blood in the esophagus may be discerned by examining the envelope. However, internal tissue is not itself marked by this procedure.

OBJECTS OF THE INVENTION

Accordingly, it is an object of the invention to provide a device and method for performing colonoscopic polypectomies that prevents or minimizes bleeding from the stalk of the polyp.

It is a further object of the invention to provide a device and method for performing colonoscopic polypectomies that does not use electricity and thus does not risk perforating the colon wall.

It is a further object of the invention to provide a device and method for performing colonoscopic polypectomies that cuts through the tissue sharply so there will be no snare entrapment or crushed destroyed tissue for the pathologist.

It is a further object of the invention to provide a device and method for performing colonoscopic polypectomies that grasps the polyp so it will not be lost.

It is a further object of the invention to provide a device and method for performing colonoscopic polypectomies that does not destroy tissue needed by a pathologist for examination.

It is a further object of the invention to provide a device and method for performing colonoscopic polypectomies that has no risk of causing a colonic explosion.

It is a further object of the invention to provide a device and method for performing colonoscopic polypectomies that marks the outside of the colon wall where the polyp had been removed on the inside of the colon wall so that if malignancy is diagnosed, the surgeon can visualize the exact part of the colon to remove.

It is a further object of the invention to provide a device and method for performing colonoscopic polypectomies that can mark the colonic wall for approximately one week.

It is a further object of the invention to provide a device and method for performing colonoscopic polypectomies that keeps the orientation of the polypectomy specimen so that a pathologist can determine where the stalk is, where the stalk was cut, and how far the malignancy is from the stalk.

BRIEF DESCRIPTION OF THE DRAWINGS

FIG. 1 shows a snare version of the present invention in an extended position.

FIG. 2 shows the snare of FIG. 1 in a retracted position.

FIG. 3 is a cross section of the wire used to form the snare of FIG. 1.

FIGS. 9a–9c show a dual clip version of the invention.

SUMMARY OF THE INVENTION

Figures 4, 5:
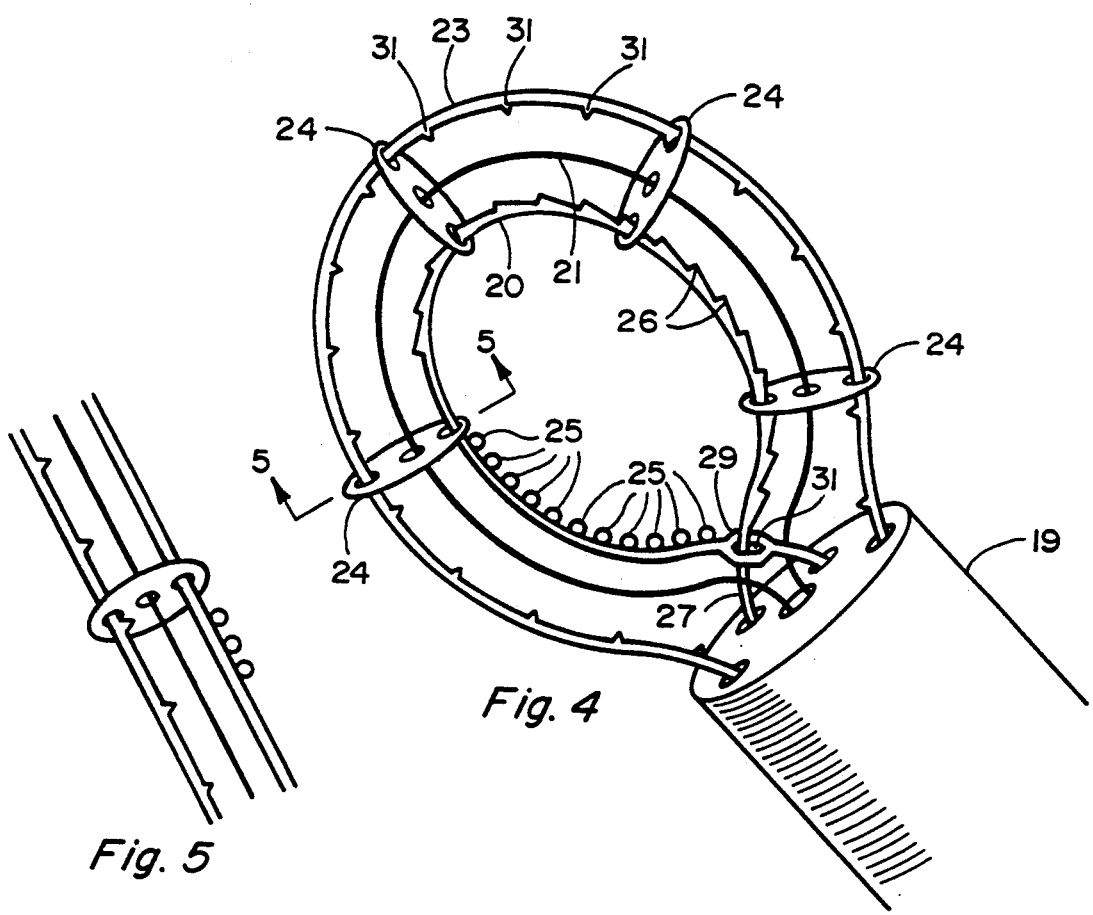
FIG. 4 is an alternate embodiment of the invention showing a snare with separate loops for marking, cutting and retaining a large polyp.
FIG. 5 is a view of a spacer for the snare of FIG. 4.

The invention comprises a surgical method and instrument such as a snare or forceps clamps, which can be moved to a position to firmly grasp a polyp. A tissue marking agent is disposed on the surface of the instrument that contacts a polyp, and the marking agent is crushed against the polyp. The marking agent is absorbed by the polyp and stains the tissue from which the polyp projects, the assist in visualizing the polyp site if conventional surgery is later required. The method and device may optionally provide for cutting and removing of the polyp and for application of a hemostatic agent to the polyp base to minimize bleeding.

DETAILED DESCRIPTION

Referring to FIG. 1, there is shown one embodiment of the invention comprising a snare comprising having a barrel or housing 11 having a distal end out of which projects wire loop 12. As shown in FIG. 3, cross section of wire loop 12 may have a recess 13 therein for deposition of marking agent 14. Marking agent 14 may comprise, for example, carbon granules or solid crushable capsule shells with a liquid marking dye, such as india ink, within the shell. A preferred marking agent includes comprises a crushable gelatin capsule containing a mixture of india ink, topical thrombin and aventine.

Marking agent 14 may be secured to wire 12 by any suitable adhesive such as plastic cement. First portion 15 of wire loop 12 is fixed with respect to housing 11, while second portion 16 of wire loop 12 is movable with respect to housing 11. Accordingly, second portion 16 may be retracted through barrel 11 to move wire loop 12 from its extended position shown in FIG. 1 to a retracted position shown in FIG. 2.

The snare shown in FIGS. 1 and 2 may be of suitable dimensions to be used in an endoscope such as a colonoscope. Accordingly, the colonoscope may be used to visualize a polyp in an internal organ of a patient, such as a colon, and the snare may be placed around the polyp. Wire loop 12 is then moved to its retracted position as shown in FIG. 2 which causes marking agents 14 to become crushed against the side of the polyp. After holding the marking agent against the polyp for a sufficient time, such as one minute, the marking agent will be removed by macrophages which in turn will go through the lymphatic channels to the lymph nodes on the serosal surface of the colon. This will stain the wall of the colon or other organ, allowing the portion of the wall to be visualized from the exterior when, for example, it is determined necessary to perform a colonic resection at a subsequent time.

It will be appreciated by those of skill in the art that various marking agents may be employed in connection with the present invention, provided the particular marking agent is absorbable by the polyp and will stain the organ from which the polyp extends for a sufficient period of time, such as one week.

FIG. 4 shows an alternate embodiment of the present invention. In this version, three loops project from housing 19, namely, marking loop 20, cutting loop 21, and retaining loop 23. Marking loop 20 and retaining loop 23 may be made of nylon or plastic. Loops 20, 21 and 23 may be optionally separated by spacing members 24, each of which comprises a structure having three apertures. The spacing of loops 20, 21 and 23 by spacing numbers 24 is shown in FIG. 5, and each loop 20, 21 and 23 is held 1-2 mm. apart. Separate spacing members 24 are approximately 1 cm. apart. Marking loop 20 contains marking agents 25 as described above. In addition, marking loop 20 includes a plurality of triangular shaped wedges 26. The distal end 19 of barrel contains five holes. Marking loop 20 passes through two holes that will be positioned closest to a polyp base, cutting loop 21 passes through one central hole, and retaining loop 23 passes through two holes on the side opposite marking loop 20.

The snare shown in FIG. 4 may be used to mark, sever, and retain a polyp in the following manner. This snare contains three separate loops 20, 21 and 23, which optionally, may be moved together. First, all three loops 20, 21 and 23 are simultaneously placed over the polyp. First loop 20 is retracted by pulling wire portion 27. It will be appreciated that first loop 20 also includes silastic structure 29 which includes an aperture so that when first loop 20 is retracted, wedges 26 ratchetedly pass through aperture 30 and thereby restrict movement of first loop 20 towards its extended position. Wire portion 27 is pulled to a point sufficient to move marking loop 20 to its retracted position and thereby crush marking agents 25 against the polyp. Cutting loop 21 is preferably made of a thin diameter metal wire suitable to sever the polyp. At first, cutting loop 21 is retracted only to an extent sufficient to be held snugly against the polyp. The next step is to retract third retaining loop 23 which contains a plurality of inwardly projecting polyp holding means 31. Holding means 31 will impale the polyp and hold it securely. Next, cutting loop 21 may be fully retracted to sever the polyp from its base. The tightness of marking loop 20 around the polyp, the sharp cut made by cutting loop 21, and the hemostatic agent all combine to minimize bleeding from the polyp stump. As cutting loop 21 is retracted further, it will sever first marking loop 20 at points 50 and 51. Marking loop 21 will be ratchetedly affixed to the stump of the polyp and may be kept in the body while housing 19, cutting and retaining loops 21 and 23, and polyp head 40 are removed.

Figure 6A:
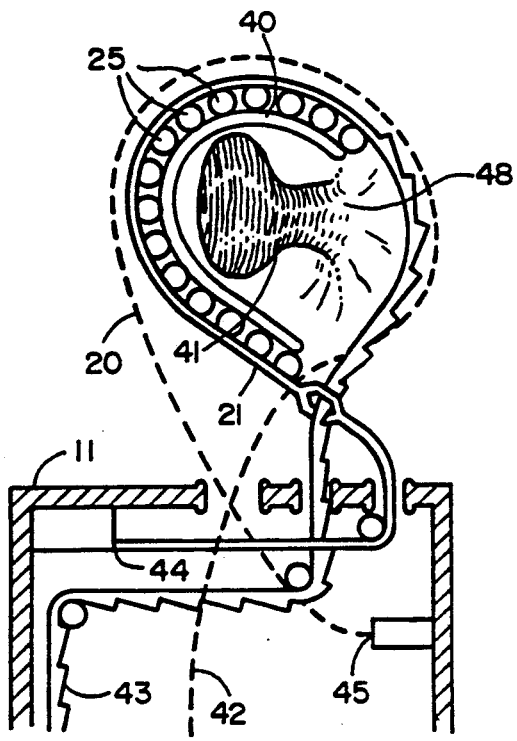
FIGS. 6a–6d show the procedure for marking and cutting a large polyp, and FIG. 6d further shows the large outer loop shown in FIGS. 4 and 5 used to snare a polyp.

The action of the marking and cutting loops is further exemplified by FIGS. 6a–6d. FIG. 6a shows marking loop 20 and cutting loop 21 being placed around a polyp. In this case, a hemostatic agent 40 has also been applied to the surface of marking agents 25, although alternatively, a hemostatic agent could be mixed with the marking agent in granules or capsules 25. A suitable hemostatic agent may comprise gelfoam, animal gelatin that has been denatured. This is usually a sponge with topical thrombin. Other suitable hemostatic agents include surgicel, which is an oxidized regenerated cellulose, or avitene, a microfibrillar collagen. Another suitable hemostatic agents include epinephrine or topical bovine thrombin, which is a liquid that converts fibrinogen to fibrin. A final suitable hemostatic agent is superstat, which is modified collagen hemin containing calcium fluoride. As shown in FIG. 6a hemostatic agent 40 is spread over marking agents 25, although in the preferred embodiment, as described above, the hemostatic agent is included with the marking agent in gelatin capsules. Loops 20 and 21 are placed over polyp 41. In the three-loop version of the invention shown in FIGS. 4 and 5, loop 23 will also be placed over the polyp. It will be appreciated that in FIG. 6a, one end of the wire forming marking loop 21 is fixed to the housing at point 44, and one end of the wire forming cutting loop 20 is also fixed to housing at point 45. Thus, each loop may be moved toward its retracted position by pulling on that portion of the wire 42, 43 not affixed to housing 11.

Figure 6B:
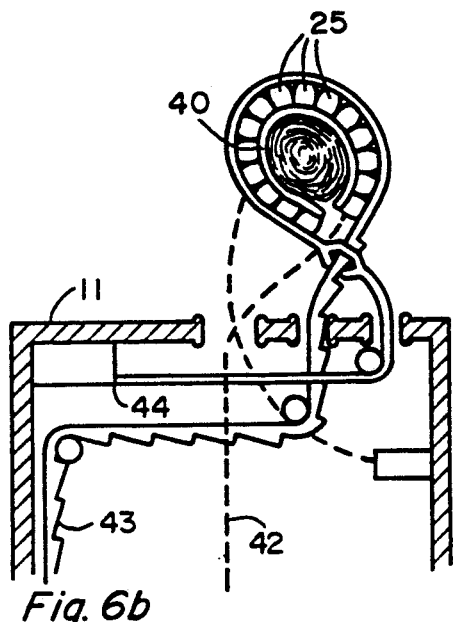
Figure 6C:
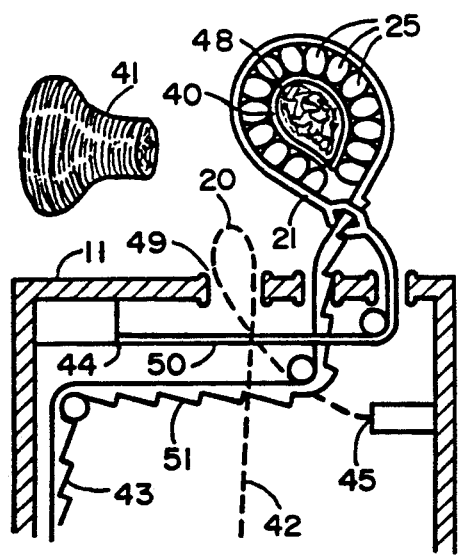
Figure 6D:
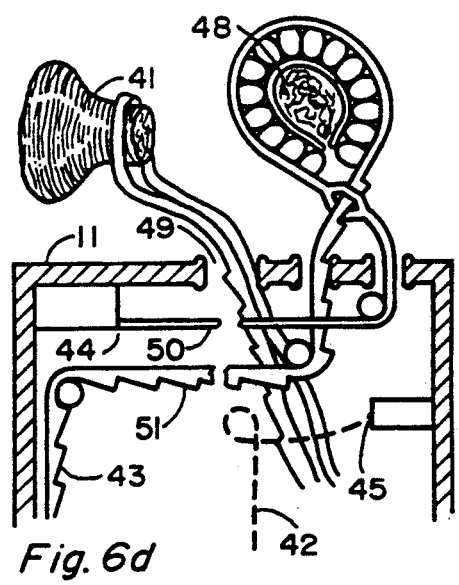

As shown in FIG. 6a, loops 20 and 21 are simultaneously placed over polyp 41. In the three-loop version of the invention shown in FIGS. 4 and 5, loop 23 will also be placed over the polyp. Loop portions 42 and 43 (and optionally, loop 23) are then pulled until they snugly surround polyp 40 as shown in FIG. 6b. At this point, loop end 43 is pulled particularly tight in order to crush marking agent 25 against polyp 41. It will further be appreciated that wedges 31 will ratchet through aperture 30 to maintain the pressure of capsules 14 against polyp 40 without a continuous pulling force on line 43. In addition, hemostatic agent 40 will engage polyp. Wire end 42 is sharply pulled causing second loop 20 to cut and sever polyp 41 from its base 48 as shown in FIG. 6c. Moreover, marking loop 21 continues to be tightly affixed to polyp base 48. Hemostatic agent 40 will be absorbed by polyp base 48 and minimize any bleeding therefrom. Finally, the movable end 42 of cutting loop 20 may be further pulled so that it passes through hole 49 in housing 11 and then cuts both wires 51 and 50, as shown in FIG. 6c. This will allow housing 11 to be retracted from the body, leaving marking loop 21 attached to polyp base 48. Polyp 41 may be subsequently retrieved with a forceps, or if the three loop version of the invention shown in FIGS. 4 and 6d is employed, polyp 41 will be held and withdrawn as housing 11 is withdrawn.

Figure 7A:
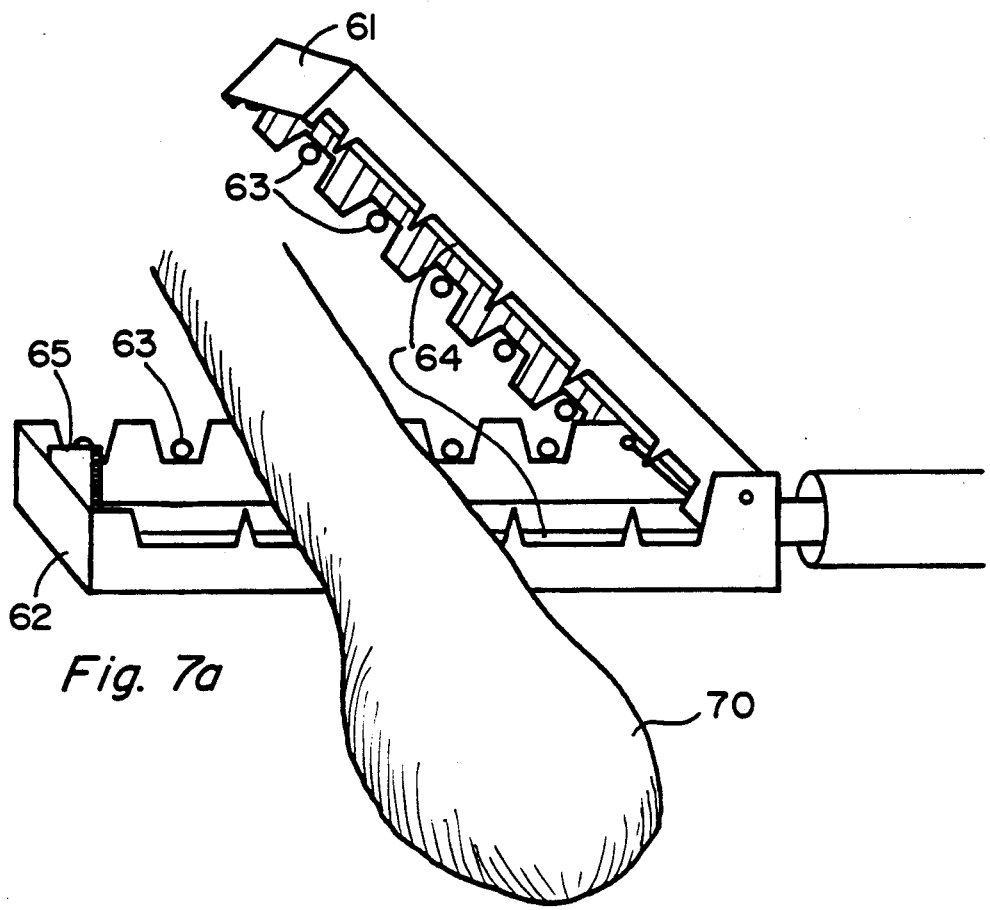
FIGS. 7a–7c show a forceps version of the present invention and its use for marking and cutting a polyp.
Figure 7B:
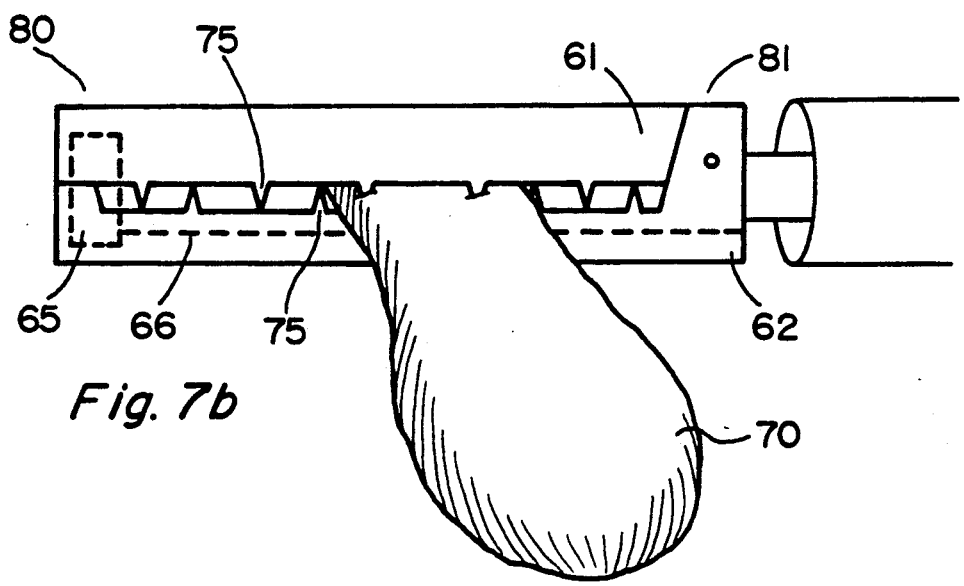
Figure 7C:
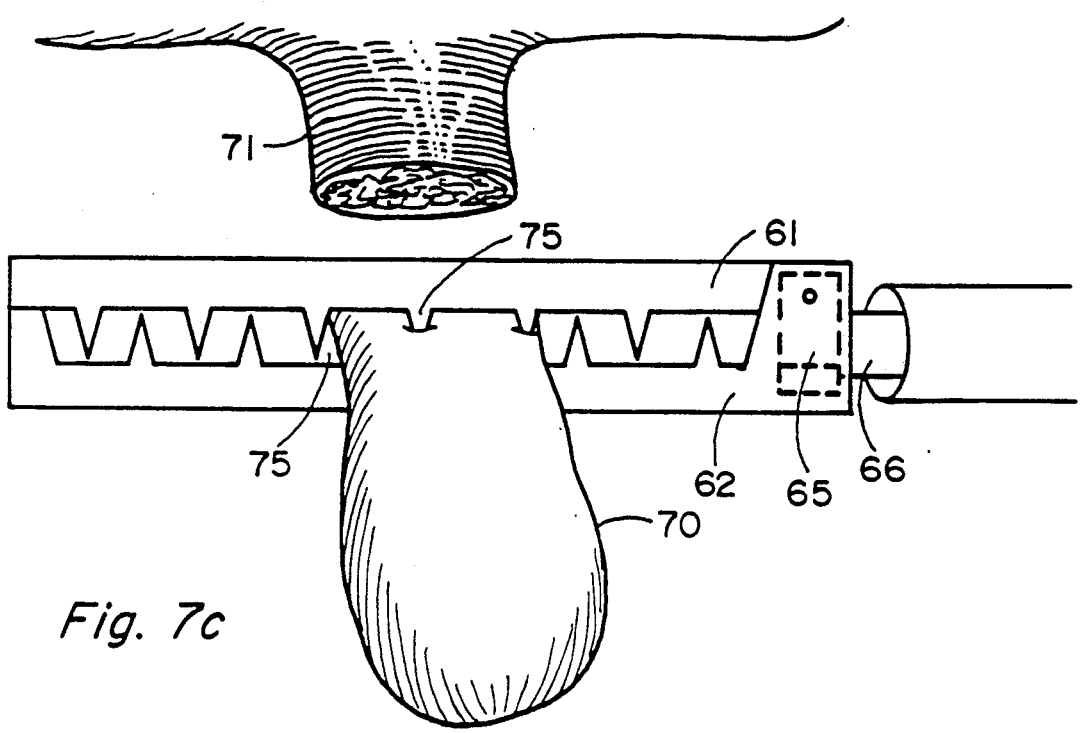

Referring now to FIGS. 7a–7c there is shown an alternate embodiment of the present invention. This embodiment comprises a modified set of forceps clamps having opposing upper 61 and lower 62 jaws. Disposed on one side of said jaws are marking agent capsules or granules as described above, which, again, may be glued to jaws 61 and 62. Each jaw is matched so as to crush the crushing agents 63 on the opposite jaw when the jaws are moved to their closed position as shown in FIG. 7b. A hemostatic agent may be applied to the surface of marking agents as described above, or preferably, included with the marking agent in gelatin capsules. The opposite side of jaws may include a pair of opposing inner blades 64, so that the polyp is severed when the jaws are closed over a polyp as shown in FIG. 7b. Alternately or optionally, blade 65 may be disposed at the distal end 80 of forceps clamp between the opposing sides of the jaws. Blade 65 is connected to wire 66 which may be pulled by the surgeon toward the opposite end 81 of jaws to thereby cut and sever polyp 70. Blade 65 may include laterally projecting flanges on each side that fit into mating grooves on the side of each jaw to form a shape similar to the tail of an airplane, to help keep blade 65 vertically disposed. As noted above, polyp 70 should not be cut until crushed marking agent 63 has had sufficient time after being crushed into polyp 70 to allow the marking agent to be absorbed by polyp base 71 as shown in FIG. 7c. Jaw teeth 75 also serve to pierce and hold polyp so it may be removed from the body simultaneously with the forceps clamps for subsequent examination.

Figure 8A:
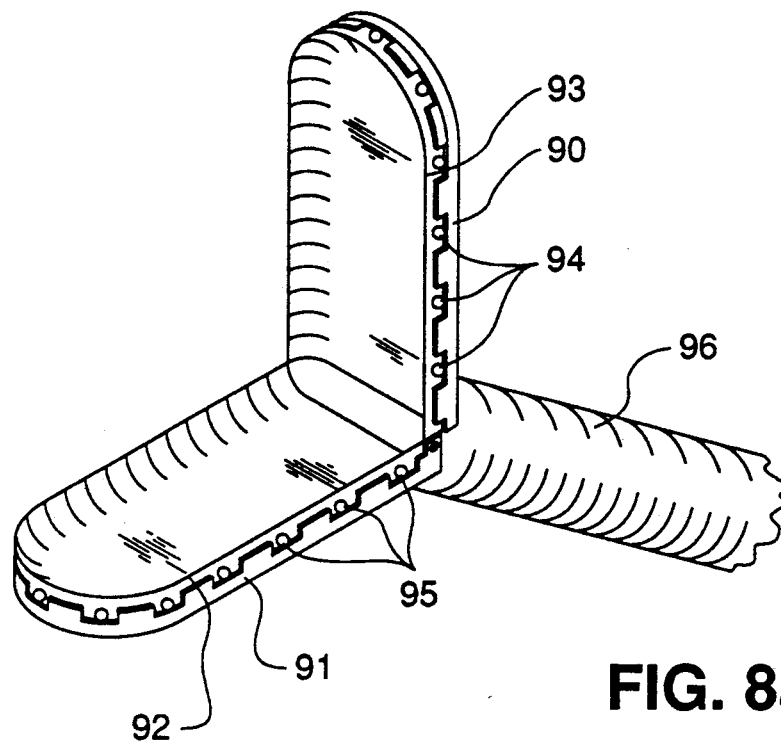
FIGS. 8a and 8b show a simple snare forceps version of the invention which can simultaneously cut and mark a polyp.
Figure 8B:
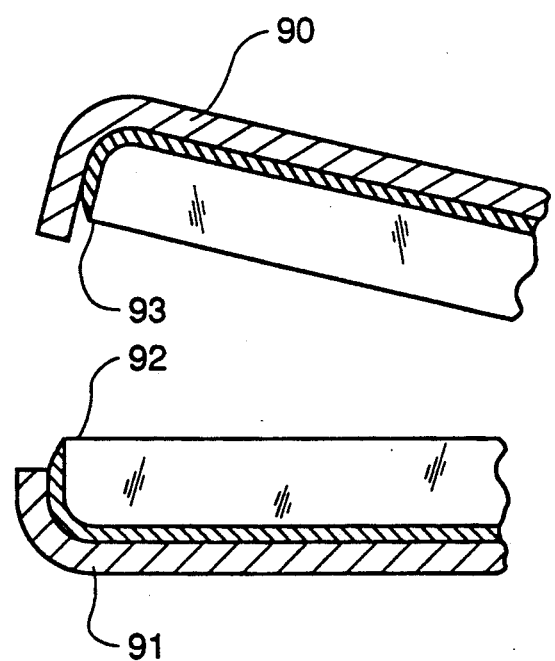

A further embodiment of the invention adapted for use with smaller polyps is disclosed in FIGS. 8a and 8b. FIG. 8a discloses a simple forceps comprising a pair of opposing jaws 90 and 91 pivotally attached to catheter 96. This construction is similar to known forceps insertable in a colonoscope channel. The interior peripheries of jaws 90 and 91 contain blades 93 and 92, which are capable severing a polyp. The outer peripheries of jaws 90 and 91 contain gelatin capsules containing a mixture of india ink, topical thrombin and aventine. When jaws 90 and 91 are pressed together, the teeth on the opposing jaw crush the capsules on the jaw, while blades 92, 93 simultaneously cut the polyp. The jaws may be held together for approximately one minute to allow marking agent to be removed by macrophages which in turn will go through the lymphatic channels to the lymph nodes on the serosal surface of the colon.

A further embodiment of the invention is disclosed in FIGS. 9a-9c. FIG. 9a shows an top view of dual clip version of the invention in a clip applicator, while FIG. 9b shows a right view of the dual clip and FIG. 9c shows a left view of the dual clip. The dual clip consists of left clip 109 and right clip 110, which are very similar to conventional Hulka clips. The two clips are joined by a common pivot pin 120. As shown in FIG. 9b, right clip 110 includes gelatin capsules 111 containing marking and hemostatic agents as described above. Capsules 111 are positioned so they will be crushed by the teeth on the opposing jaw. Metal clamps 102 fit in matching grooves on the top and bottom surfaces of clips 109 and 110. When the metal clamps are forced toward the tips 107 of clips 109, 110, they will force the opposing jaws to move against each other and the clamps will snap into recesses 106.

A vertically extending blade 103 is positioned intermediate clips 109, 110, and is held in such vertical position be lateral wings, similar to the wings shown in FIGS. 7a and 7b. One of such lateral wings is permanently attached to left clip 109 as it extends completely through slot 115 in clip 109, and is held in place by widened portion 104. To use this version of the invention, the dual clip is placed in the tip of applicator 100, which may be a conventional Hulka clip applicator. The jaws of the clips are then placed around the polyp to be removed, with clip 110 (containing the marking agent) placed on the side toward the colon wall. Plunger 101 of applicator 100 is then depressed to force clamps 102 toward clip tips 107 to close and clamp the clips shut. The polyp will be secured to left clip 109, and right clip 110 will be secured to the base of the polyp to mark the polyp. Wire 121 is then retracted, which pulls blade 103 toward plunger 101, severing the polyp from its base. As may be appreciated by viewing slot 115 in FIG. 9c, blade 103 may continue to be retracted backward until it also severs plastic pivot pin 120. This severance allows left clip 109 to separate from right clip 110. Therefore, applicator may be withdrawn from the colon along with blade 103 and left clip 109, which holds the severed polyp. Right clip will remain in the colon clamped to the polyp base, and will eventually pass out of the body.

It will appreciated by those of skill in the art that the foregoing systems provide a mechanism for easily marking the location of a polyp in an internal organ, while also permitting the polyp to be removed without losing the polyp, and while simultaneously applying a hemostatic agent to minimize bleeding. Moreover, the polyp is retrieved intact so as to be available for subsequent analysis.

I claim:

1. A surgical polyp marking snare comprising:
   a housing,
   a first wire loop extending from the housing,
   a crushable tissue marking agent disposed on the wire loop,
   the wire loop being movable between an extended position in which the loop may be placed over a polyp, and a retracted position in which the size of the loop is reduced to thereby crush the marking agent against the polyp, and
   means to move the wire loop between the extended and retracted positions.

2. The surgical polyp marking snare of claim 1 wherein the tissue marking agent comprises carbon granules.

3. The surgical polyp marking snare of claim 1 wherein the tissue marking agent comprises a solid crushable capsule shell with a liquid marking dye within the shell.

4. The surgical polyp marking snare of claim 1 wherein a first portion of the loop is fixed with respect to the housing and a second portion of the loop is movable with respect to the housing, the tissue marking agent being disposed on the wire loop between the fixed and movable portions, and wherein the loop is movable between the extended and retracted positions by moving the movable portion toward the housing.

5. The surgical polyp marking snare of claim 1 further comprising first and second sides of the wire loop, the tissue marking agent being disposed on the wire loop between the first and second sides, the loop being movable from the extended to the retracted position by simultaneously pulling the first and second sides toward the housing.

6. The surgical polyp marking snare of claim 1 wherein the tissue marking agent is disposed in a recess in the first wire loop.

7. The surgical polyp marking snare of claim 1 wherein the wire loop is metal.

8. The surgical polyp marking snare of claim 1 further comprising a topical hemostatic agent disposed on the wire loop, such that the hemostatic agent may contact a polyp when the wire loop is moved against the polyp.

9. The surgical polyp marking snare of claim 8 wherein the topical hemostatic agent is selected from the group consisting of denatured animal gelatin, topical thrombin, epinephrine, oxidized regenerated cellulose, microfibrillar collagen or modified collagen hemin comprising calcium fluoride.

10. The surgical polyp marking snare of claim 1 further comprising a structure having an aperture, the first loop passing through the aperture,
a plurality of wedges extending from the first loop, such that when the first loop is moved towards its retracted position, the wedges ratchetedly pass through the aperture to thereby restrict movement of the first loop toward the extended position.

11. The surgical polyp marking snare of claim 1 further comprising:
a second cutting wire loop adjacent to the first wire loop such that both loops may be simultaneously placed over a polyp, the second wire loop being movable between extended and retracted positions,
such that when the second loop is moved toward its retracted position it may sever the polyp.

12. The surgical polyp marking snare of claim 11, wherein the second cutting wire loop traverses the first wire loop, such that the second cutting wire loop may sever the first wire loop when moved towards its retracted position.

13. The surgical polyp marking snare of claim 11, further comprising a third wire loop adjacent to the second wire loop and on the side of the second wire loop opposite the first wire loop, the third wire loop being movable between extended and retracted positions,
the third wire loop comprising at least one inwardly projecting polyp holding means.

14. The surgical polyp marking snare of claim 13 further comprising at least one spacing member having three apertures, the first, second and third loops passing through one respective aperture to thereby space the loops apart from each other.

15. The surgical polyp marking snare of claim 13 wherein the first loop is comprised of metal, and the second and third loops are comprised of a material selected from the group of polymeric silicone or plastic.

16. A surgical polyp marking forceps comprising:
a pair of opposing jaws adapted to close an anatomical structure therebetween, the jaws being insertable into a human colon,
means to close the jaws,
a crushable tissue marking agent disposed on at least one of the jaws and a marking agent crushing means on the opposite jaw, such that the crushing means crushes the marking agent when the jaws are closed.

17. The surgical polyp marking forceps of claim 16 further comprising upper and lower opposing blades adjacent to the jaws, such that tissue between the blades is cut when the jaws are closed.

18. The surgical polyp marking forceps of claim 16 further comprising first and second ends of the jaws, and a blade adjacent the jaws movable between from the first jaw end toward the second jaw end to thereby cut tissue located between the ends.

19. The surgical polyp marking forceps of claim 16 wherein the tissue marking agent comprises carbon granules.

20. The surgical polyp marking forceps of claim 16 wherein the tissue marking agent comprises a solid crushable capsule shell with a liquid marking dye within the shell.

21. The surgical polyp marking forceps of claim 16 further comprising a topical hemostatic agent disposed on at least one of the jaws, such that the hemostatic agent may contact a polyp when the jaws are closed.

22. The surgical polyp marking snare of claim 21 wherein the topical hemostatic agent is selected from the group consisting of denatured animal gelatin, topical thrombin, epinephrine, oxidized regenerated cellulose, microfibrillar collagen or modified collagen hemin comprising calcium fluoride.

23. A method for marking a polyp, comprising the steps of:
providing a device for crushing a crushable tissue marking agent against the polyp,
crushing the tissue marking agent against the polyp, and
holding the crushed tissue marking agent against the polyp until the marking agent is lymphatically absorbed by the polyp and carried to the base of the polyp.

24. The method of claim 23 wherein the crushing device comprises a snare.

25. The method of claim 23 wherein the crushing device comprises a forceps clamp.

26. The method of claim 23 wherein the tissue marking agent comprises carbon granules.

27. The method of claim 23 wherein the tissue marking agent comprises a solid crushable capsule shell with a liquid marking dye within the shell.

28. The method of claim 23 further comprising the step of severing the polyp from the tissue from which it projects.

29. The method of claim 23 further comprising the step of applying a topical hemostatic agent to the polyp.

30. The method of claim 29 wherein the topical hemostatic agent is selected from the group consisting of denatured animal gelatin, topical thrombin, epinephrine, oxidized regenerated cellulose, microfibrillar collagen or modified collagen hemin comprising calcium fluoride.

* * * * *